(12) United States Patent
Martin et al.

(10) Patent No.: US 10,143,818 B2
(45) Date of Patent: Dec. 4, 2018

(54) DUAL-CONNECTOR WYE PIECE

(71) Applicant: Fisher & Paykel Healthcare Limited, Auckland (NZ)

(72) Inventors: Madeleine Bess Martin, Auckland (NZ); David Robert Kemps, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 673 days.

(21) Appl. No.: 14/762,755

(22) PCT Filed: Jan. 21, 2014

(86) PCT No.: PCT/NZ2014/000007
§ 371 (c)(1),
(2) Date: Jul. 22, 2015

(87) PCT Pub. No.: WO2014/116122
PCT Pub. Date: Jul. 31, 2014

(65) Prior Publication Data
US 2015/0352310 A1  Dec. 10, 2015

Related U.S. Application Data

(60) Provisional application No. 61/755,300, filed on Jan. 22, 2013.

(51) Int. Cl.
*A61M 16/08* (2006.01)
*A61M 16/12* (2006.01)
*A61M 16/00* (2006.01)

(52) U.S. Cl.
CPC .... *A61M 16/0833* (2014.02); *A61M 16/0841* (2014.02); *A61M 16/0858* (2014.02); *A61M 16/12* (2013.01); *A61M 2016/0027* (2013.01)

(58) Field of Classification Search
CPC .......... A61M 16/0816; A61M 16/0833; A61M 16/0841; A61M 16/0858; A61M 16/0057;
(Continued)

(56) References Cited

U.S. PATENT DOCUMENTS 4,723,543 A    2/1988  Beran
5,195,980 A *  3/1993  Catlin ............... A61M 39/0693
                                                   604/167.04
(Continued)

FOREIGN PATENT DOCUMENTS

DE   202011107902 U1 *  1/2012  ........ A61M 16/0816
FR   2725627              10/1994

OTHER PUBLICATIONS

Machine translation of DE 202011107902 U1.*
(Continued)

*Primary Examiner* — (Jackie) Tan-Uyen T Ho
*Assistant Examiner* — Joseph D Boecker
(74) *Attorney, Agent, or Firm* — Knobbe, Martens, Olson & Bear, LLP (57) ABSTRACT

A wye connector has a patient coupling end. The patient coupling end has a first connector surface and a second connector surface. The first connector surface has a first diameter at an axial location along the patient coupling end. The second connector surface has a second diameter at the same axial location along the patient coupling end. The first diameter is larger than the second diameter. The second connector surface projects axially outward beyond the first connector surface.

22 Claims, 12 Drawing Sheets (58) Field of Classification Search
CPC .............. A61M 16/04; A61M 16/0463; A61M 16/0486; A61M 16/06; A61M 16/08; A61M 16/10; A61M 16/12
USPC ........ 128/202.27; 403/217; 285/131.1, 132.1
See application file for complete search history.

(56) References Cited

U.S. PATENT DOCUMENTS

| | | | |
|---|---|---|---|
| 5,228,436 A * | 7/1993 | Parkin | A61M 16/0833 128/203.12 |
| D362,503 S | 9/1995 | Cook et al. | |
| 5,776,117 A * | 7/1998 | Haselhorst | A61M 39/10 604/533 |
| 6,209,539 B1 * | 4/2001 | Loescher | A61M 16/08 128/204.17 |
| D492,030 S | 6/2004 | Rani | |
| D492,773 S | 7/2004 | Elllingboe et al. | |
| D519,632 S | 4/2006 | Bayron et al. | |
| D547,447 S | 7/2007 | Bruce et al. | |
| 7,634,998 B1 | 12/2009 | Fenley | |
| D649,240 S | 11/2011 | Lewis et al. | |
| D672,459 S | 12/2012 | Miller | |
| D685,906 S | 7/2013 | Dale et al. | |
| D689,187 S | 9/2013 | Kruger | |
| D691,717 S | 10/2013 | McLean et al. | |
| D709,612 S | 7/2014 | Lewis | |
| D723,681 S | 3/2015 | Ingram et al. | |
| 2008/0077063 A1 * | 3/2008 | Meyer | A61H 9/0078 601/148 |
| 2009/0105692 A1 | 4/2009 | Lopez et al. | |
| 2010/0071688 A1 * | 3/2010 | Dwyer | A61M 16/0816 128/200.18 |
| 2010/0071695 A1 | 3/2010 | Thiessen | |
| 2010/0163022 A1 | 7/2010 | Brewer et al. | |
| 2010/0163051 A1 * | 7/2010 | Brewer | A61M 16/0463 128/207.14 |
| 2011/0088696 A1 * | 4/2011 | Ratner | A61M 16/0816 128/205.24 |
| 2012/0180791 A1 * | 7/2012 | Ciccone | A61M 16/0463 128/204.18 |
| 2015/0021909 A1 * | 1/2015 | Gulliver | A61M 16/0666 285/319 |
| 2017/0246417 A1 * | 8/2017 | Kemps | A61M 16/0833 |

OTHER PUBLICATIONS

International Search Report for PCT/NZ2014/000007 dated Jun. 26, 2014 in 3 pages.
International Preliminary Report on Patentability in corresponding International Patent Application No. PCT/NZ2014/000007, dated Aug. 6, 2015, in 7 pages.

* cited by examiner

DUAL-CONNECTOR WYE PIECE

INCORPORATION BY REFERENCE TO ANY PRIORITY APPLICATIONS

This application is a national phase of International Application No. PCT/NZ2014/000007, filed Jan. 21, 2014, which claims the priority benefit of U.S. Provisional Patent Application No. 61/755,300, filed on Jan. 22, 2013, which is hereby incorporated by reference in its entirety.

BACKGROUND OF THE INVENTION

Field of the Invention

The present invention generally relates to a patient wye for use in connecting medical respiration or ventilation systems. More particularly, the present invention relates to a patient wye in which the patient end is configured for separate mating with two different components.

Description of the Related Art

A ventilator is a machine designed to mechanically move breathable air into and out of the lungs. The ventilator provides the mechanism of breathing for a patient who is physically unable to breathe or who is breathing insufficiently.

A breathing circuit connects the ventilator to a patient interface, such as an endotracheal tube or a mask, for example but without limitation. The breathing circuit can include an inspiratory conduit and an expiratory conduit. The inspiratory conduit delivers breathing gases while the expiratory conduit returns gases to the ventilator.

SUMMARY OF THE INVENTION

A wye connects the inspiratory conduit and the expiratory conduit to a patient outlet, which can be joined to a patient interface (possibly through an additional short conduit). In some configurations, the wye includes a standard 22 mm taper male connector to couple the patient outlet of the wye to mask-style interfaces. In some configurations, the wye includes a standard 15 mm taper female connector to couple the patient outlet of the wye to endotracheal tube-style interfaces. In some configurations, the wye includes both the standard 15 mm taper female connector and the standard 22 mm taper male connector.

Applicant has found, however, that wyes with both connectors generally have both connectors (i.e., the 15 mm female and the 22 mm male) terminating at the same axial location. Thus, such wyes result in the female connector being shrouded by the male connector. With a shrouded female connector, the medical professional making connections may become confused regarding how to make the connections with the 15 mm male connector at the end of the endotracheal component. Accordingly, one aspect of the present invention relates to the recognition that having an enshrouded female connector that does not protrude beyond the male connector can cause issues with making a proper connection of components.

It is therefore an object of certain features, aspects and advantages of the present invention to provide a wye connector that overcomes or at least ameliorates one or more of the disadvantages of the prior art, or alternatively at least provides the public or industry with a useful choice.

Further objects of the invention may become apparent from the following description.

Accordingly, a wye connector that is arranged and configured in accordance with certain features, aspects and advantages of the present invention can include a body with a patient end, an inspiratory end and an expiratory end in which the patient end includes a male connector that encircles a female connector and in which the female connector protrudes beyond the male connector.

In some configurations, a wye connector comprises a patient coupling end. The patient coupling end has a first connector surface and a second connector surface. The first connector surface has a first diameter at an axial location along the patient coupling end. The second connector surface has a second diameter at the same axial location along the patient coupling end. The first diameter is larger than the second diameter. At least a portion of the second connector surface projects axially outward beyond the first connector surface.

In some such configurations, the first connector surface is formed on a first connector portion and the second connector surface is formed on a second connector portion with the first connector portion and the second connector portion being separated by a gap.

In some such configurations, the first connector surface terminates proximally of the gap.

In some such configurations, the gap is isolated from flow through the patient coupling end of the wye connector.

In some such configurations, the first connector surface comprises a male taper connector and the second connector surface comprises a female taper connector.

In some such configurations, the male taper connector is a 22 mm male taper connector and the female taper connector is a 15 mm female taper connector.

In some configurations, the wye connector further comprises an inspiratory connector end and an expiratory connector end with the inspiratory connector end defining at least a portion of an inspiratory branch and the expiratory connector end defining at least a portion of an expiratory branch.

In some such configurations, the inspiratory connector end defines an inspiratory flow lumen having an inspiratory flow lumen axis and the expiratory connector end defines an expiratory flow lumen having an expiratory flow lumen axis with the inspiratory flow lumen axis and the expiratory flow lumen axis extending generally parallel to each other.

In some such configurations, the wye connector further comprises a probe port positioned between the inspiratory connector end and the patient coupling end.

In some such configurations, the probe port is positioned along the inspiratory branch.

In some configurations, the wye connector further comprises an introduction port positioned between the inspiratory connector end and the patient coupling end.

In some such configurations, the introduction port is positioned between the inspiratory branch and the expiratory branch.

BRIEF DESCRIPTION OF THE DRAWINGS

These and other features, aspects and advantages of the present invention will be described with reference to the following drawings.

DETAILED DESCRIPTION OF THE PREFERRED EMBODIMENTS

Figure 1:
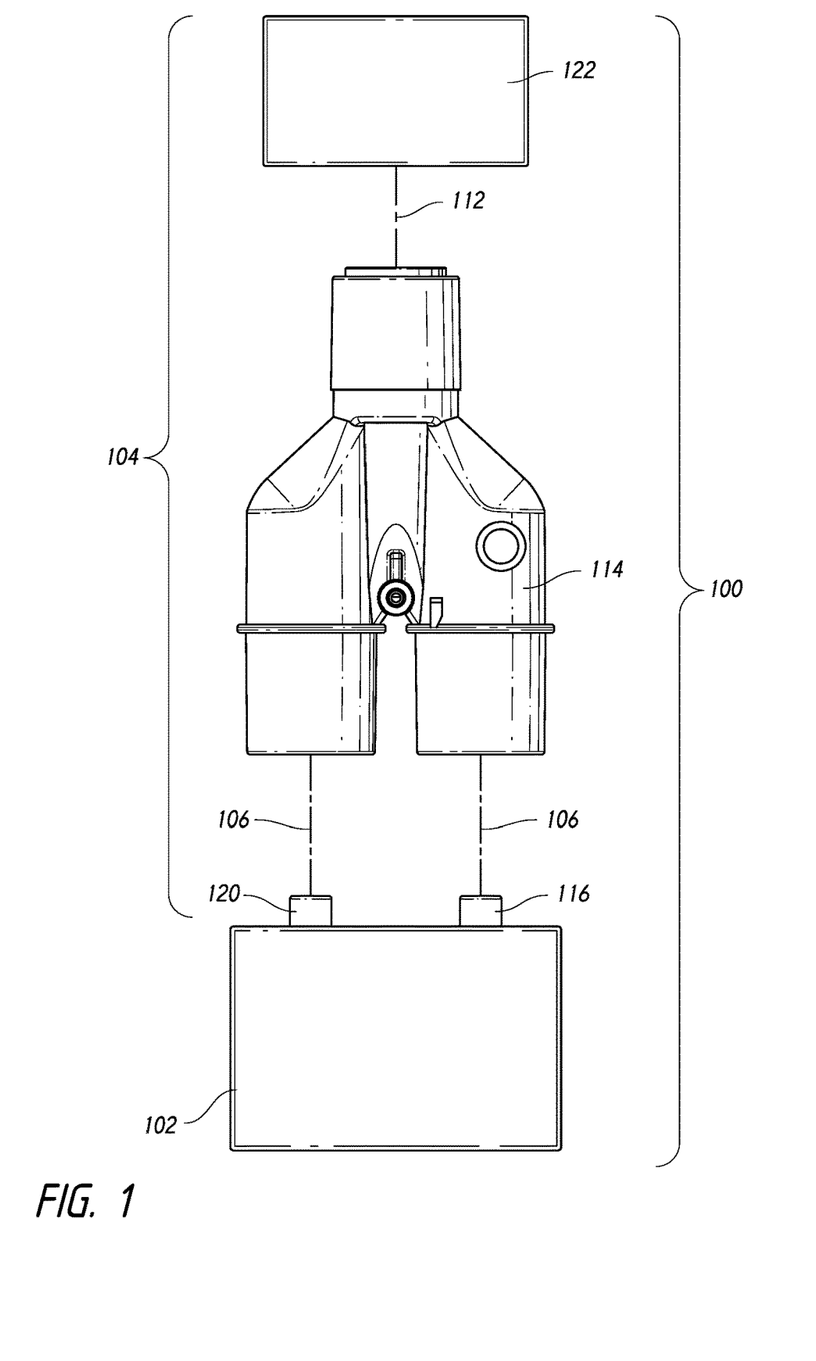
FIG. 1 is a schematic representation of a mechanical ventilation system that can be used with a wye connector that is arranged and configured in accordance with certain features, aspects and advantages of the present invention.

With reference initially to FIG. 1, a mechanical ventilation system 100 is schematically illustrated. In general, the system 100 comprises a ventilator 102 connected to a patient circuit 104.

The patient circuit 104 can comprise an inspiratory limb 106, an expiratory limb 110 and a patient limb 112. The inspiratory limb 106, the expiratory limb 110 and the patient limb 112 can be connected to one another by a patient wye 114. The inspiratory limb 106 and the expiratory limb 110 respectively connect the patient wye 114 to a supply port 116 and a return port 120 of the ventilator 102 in the illustrated configuration.

The patient limb 112 connects the patient wye 114 to a patient interface 122. In some configurations, the patient interface 122 can be used for invasive ventilation and, in such configurations, the patient wye 114 can be configured to connect to a tracheotomy tube or an endotracheal tube, for example. In some configurations, the patient interface 122 can be used for noninvasive ventilation and, in such configurations, the patient can include a breathing mask, such as a nasal mask, an oral mask, an oral-nasal mask, a nasal cannula or the like. As will be described, the patient wye 114 can be configured to include a plurality of connectors used to connect to different interfaces 122.

The ventilator 102 generally operates to provide a supply of breathing gas to the inspiratory limb 106 for delivery to the patient interface 122 via the patient wye 114 and the patient limb 112. The ventilator 102 may receive exhaled air from the patient that is delivered to an exhalation valve or similar device on the ventilator. The exhaled air may pass from the patient interface 122, through the patient limb 112, through the patient wye 114 and through the expiratory limb 110.

Figure 2:
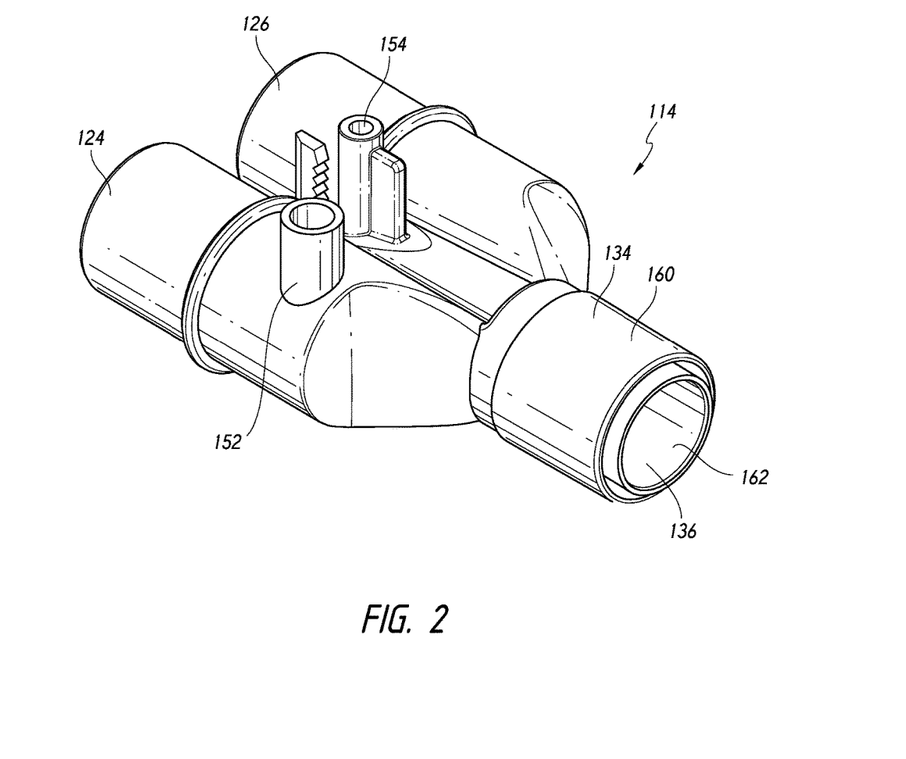
FIG. 2 is a perspective view of a wye connector that is arranged and configured in accordance with certain features, aspects and advantages of the present invention.
Figure 3:
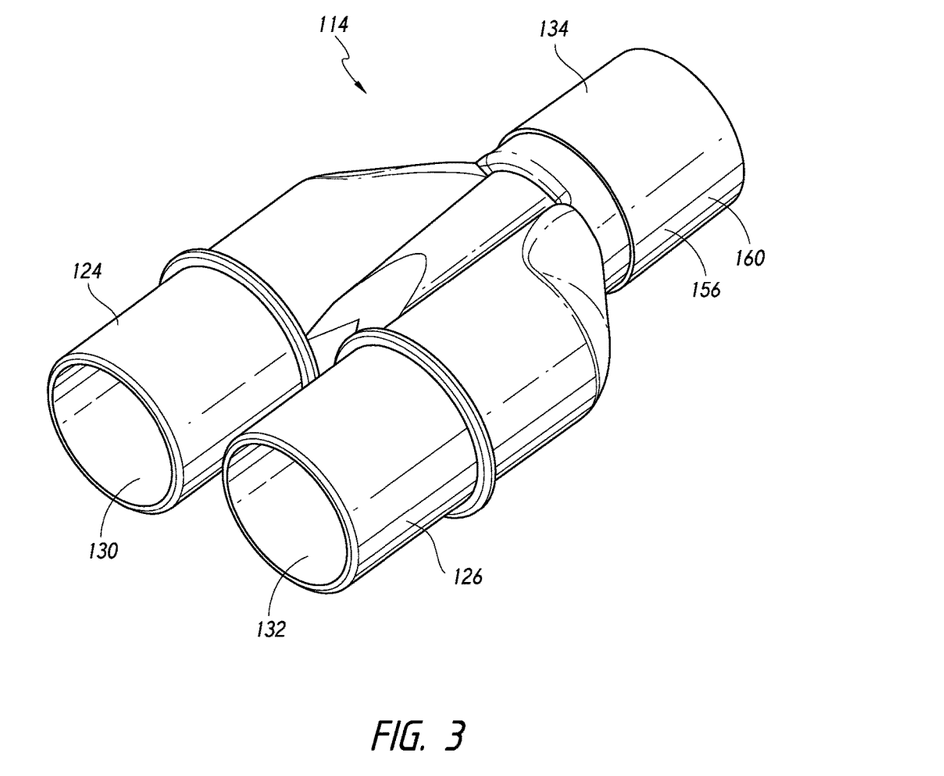
FIG. 3 is another perspective view of the wye connector of FIG. 2.
Figure 4:
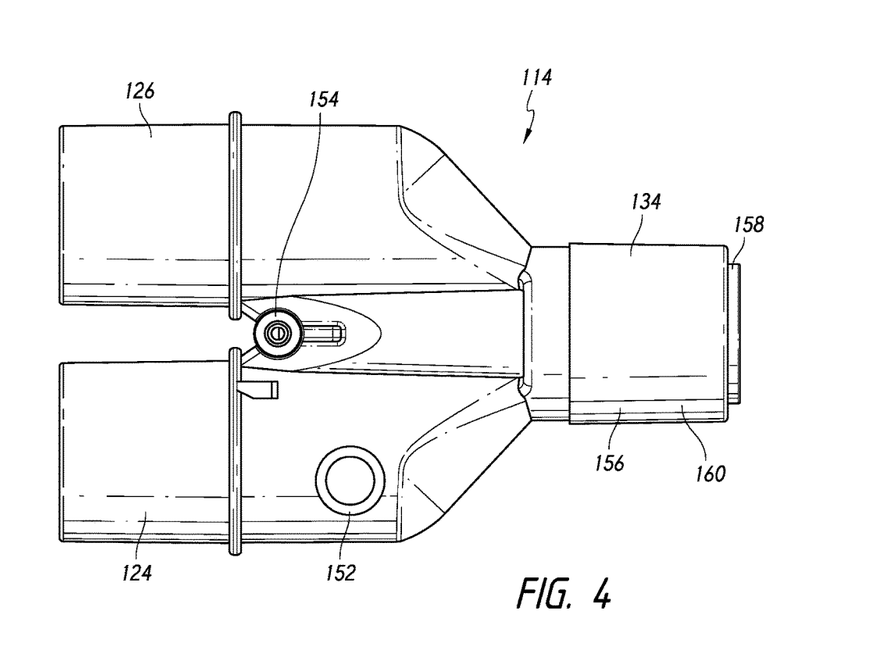
FIG. 4 is a top view of the wye connector of FIG. 2.
Figure 5:
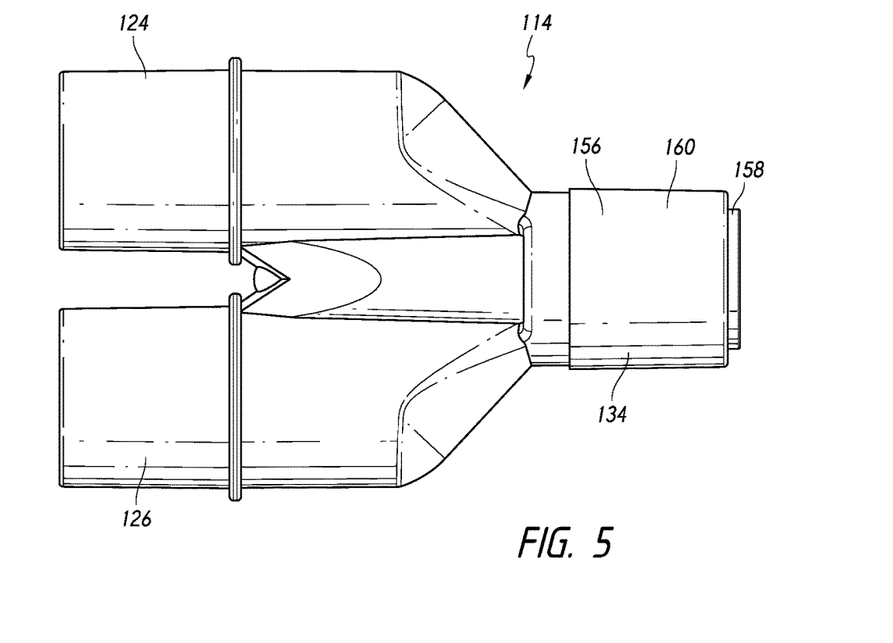
FIG. 5 is a bottom view of the wye connector of FIG. 2.
Figure 6:
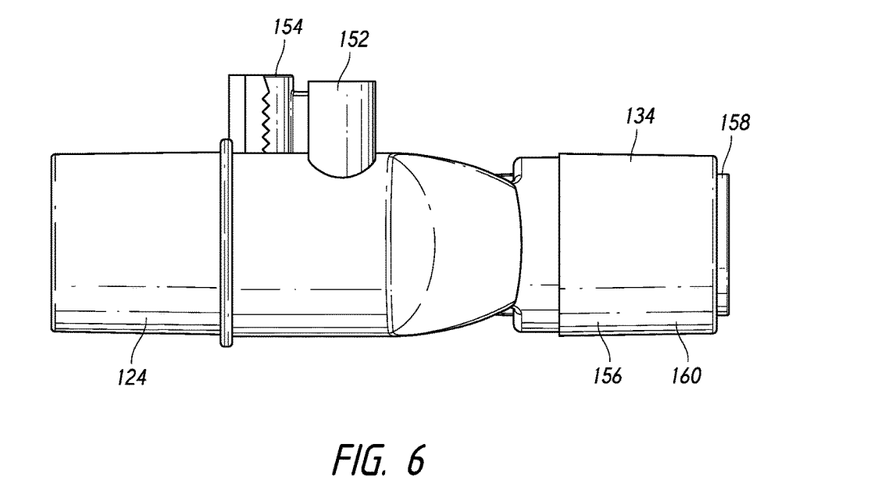
FIG. 6 is a left side view of the wye connector of FIG. 2.
Figure 7:
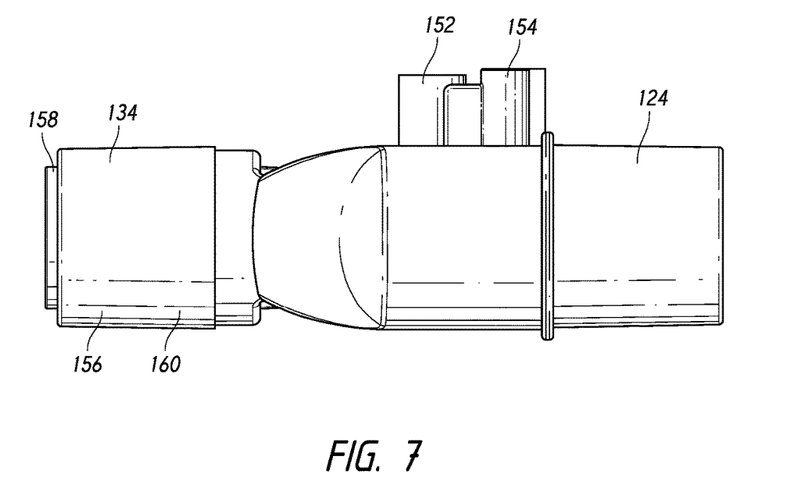
FIG. 7 is a right side view of the wye connector of FIG. 2.
Figure 8:
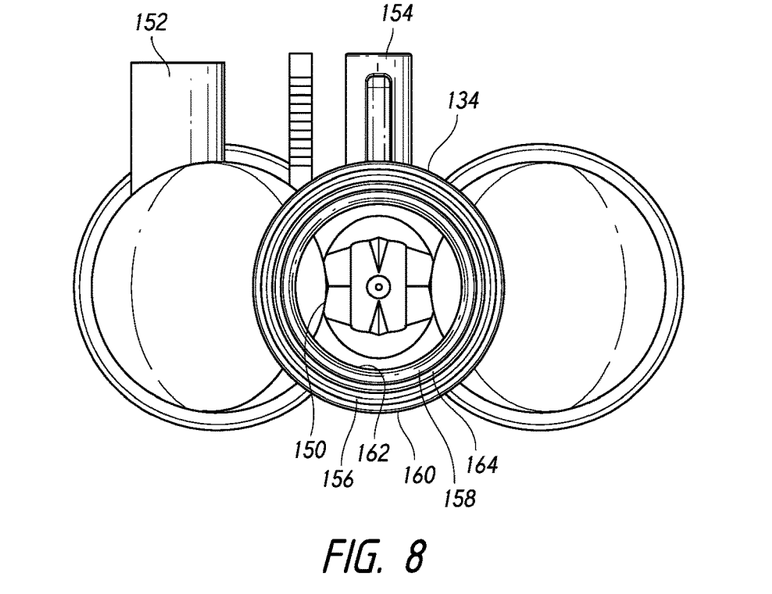
FIG. 8 is a front view of the wye connector of FIG. 2.
Figure 9:
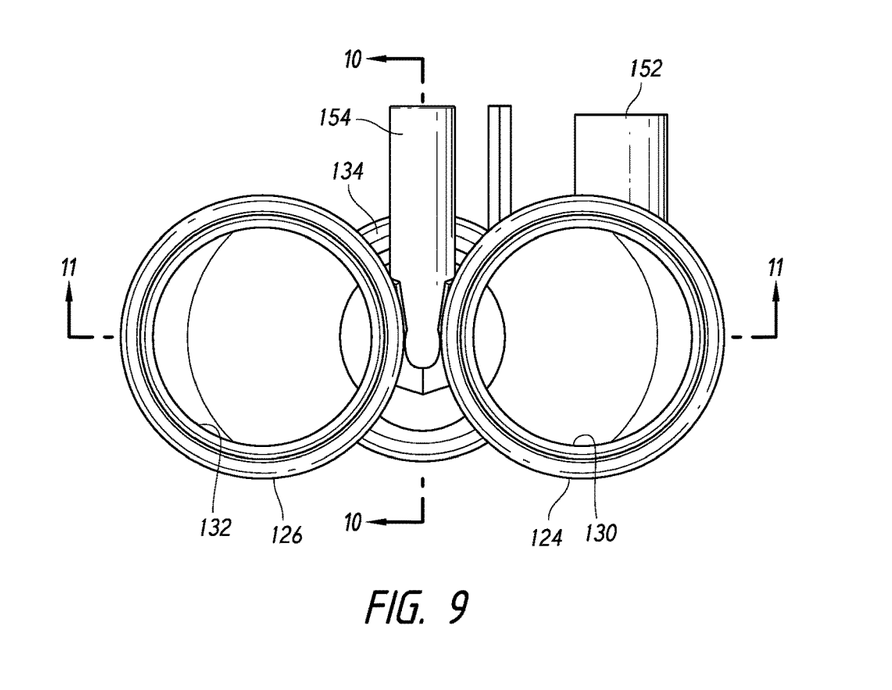
FIG. 9 is a rear view of the wye connector of FIG. 2.
Figure 12:
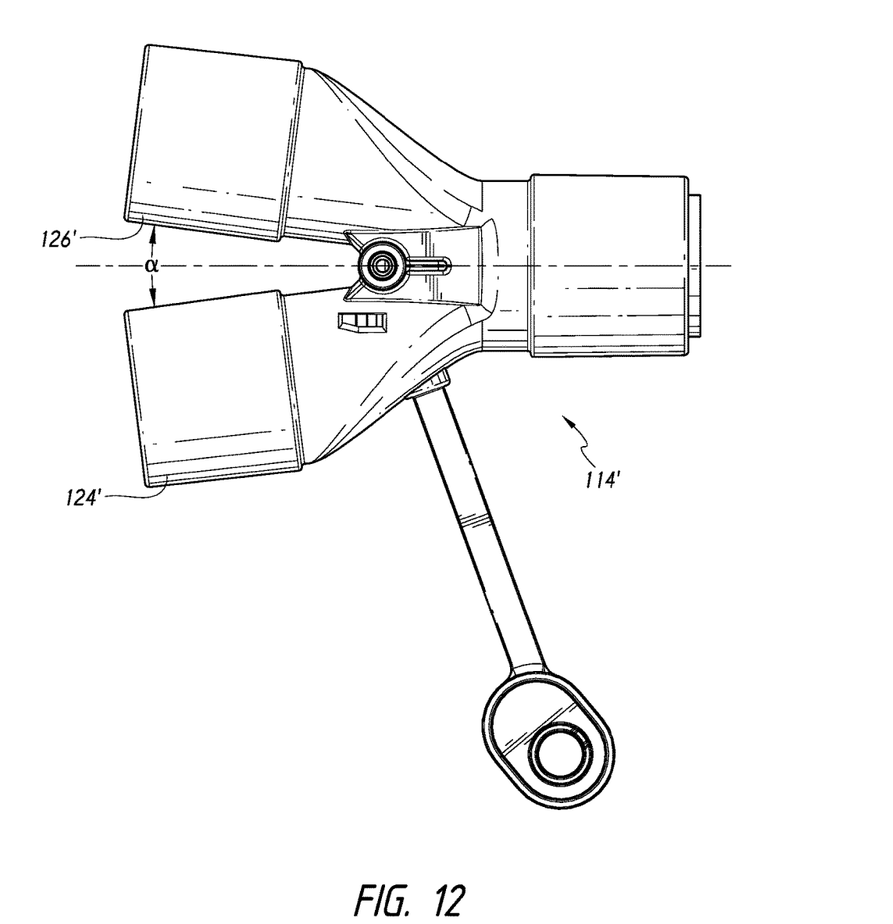
FIG. 12 is a top view of another wye connector that is arranged and configured in accordance with certain features, aspects and advantages of the present invention.
Figure 13:
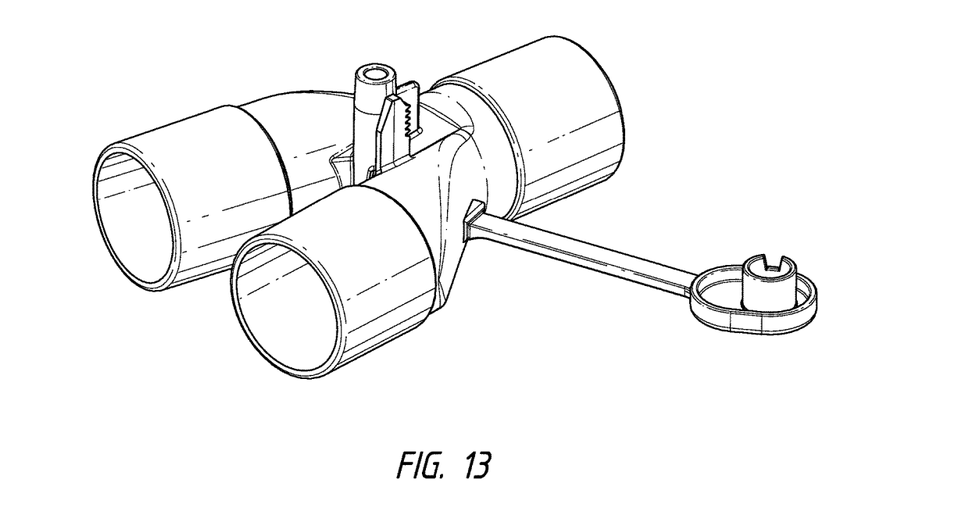
FIG. 13 is a perspective view of the wye connector of FIG. 12.
Figure 14:
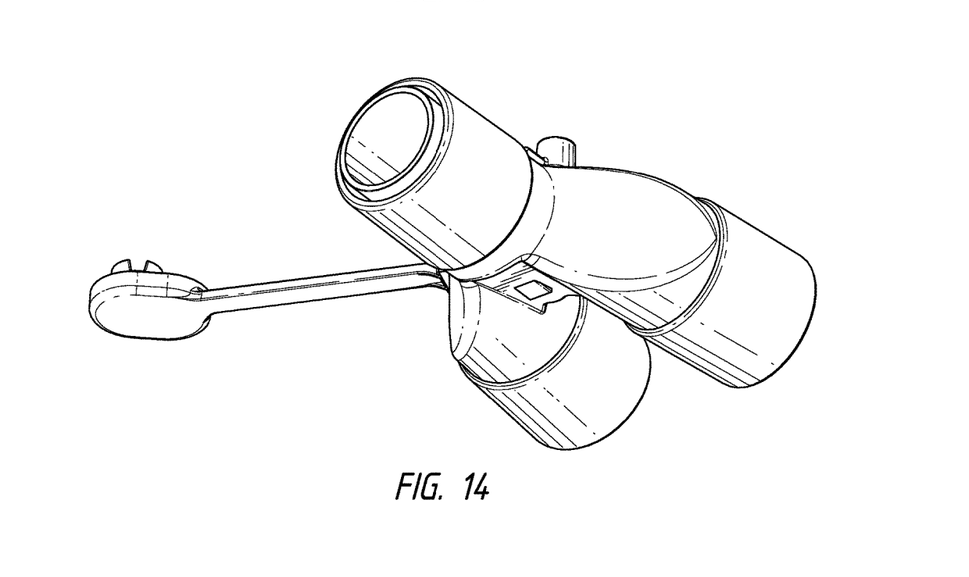
FIG. 14 is another perspective view of the wye connector of FIG. 12.
Figure 15:
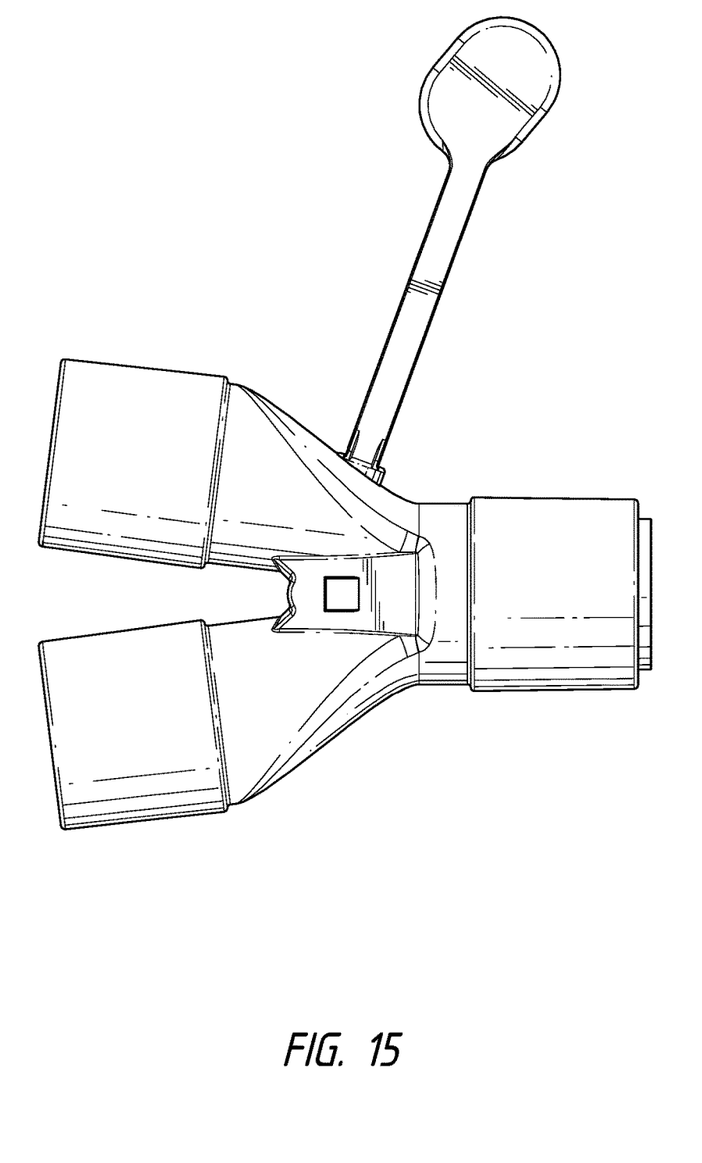
FIG. 15 is a bottom view of the wye connector of FIG. 12.
Figure 16:
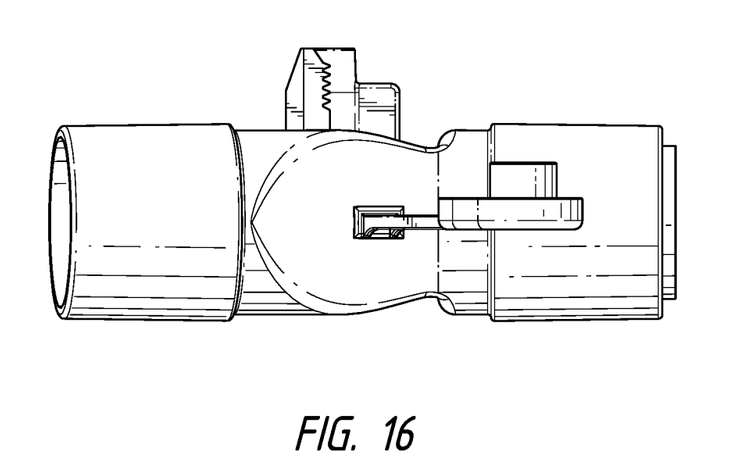
FIG. 16 is a first side view of the wye connector of FIG. 12.
Figure 17:
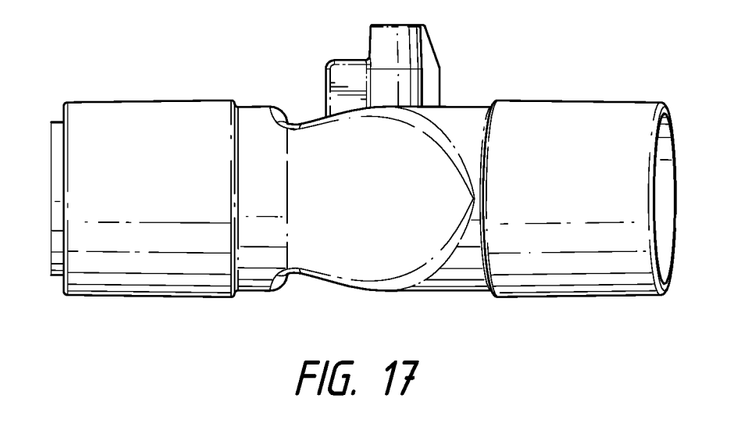
FIG. 17 is a second side view of the wye connector of FIG. 12.
Figure 18:
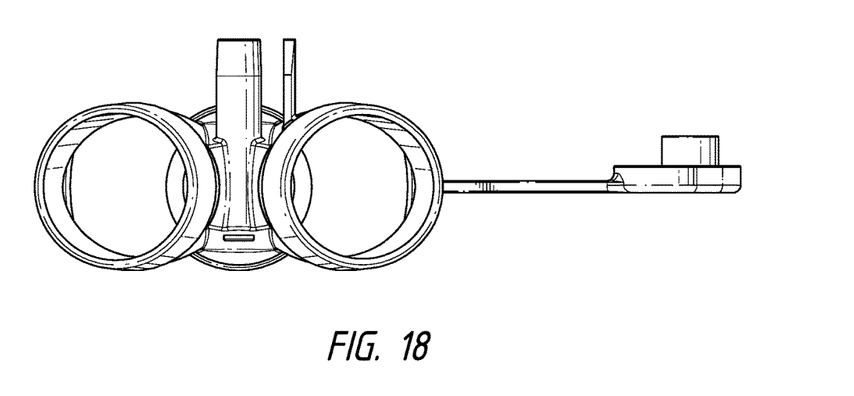
FIG. 18 is a first end view of the wye connector of FIG. 12.
Figure 19:
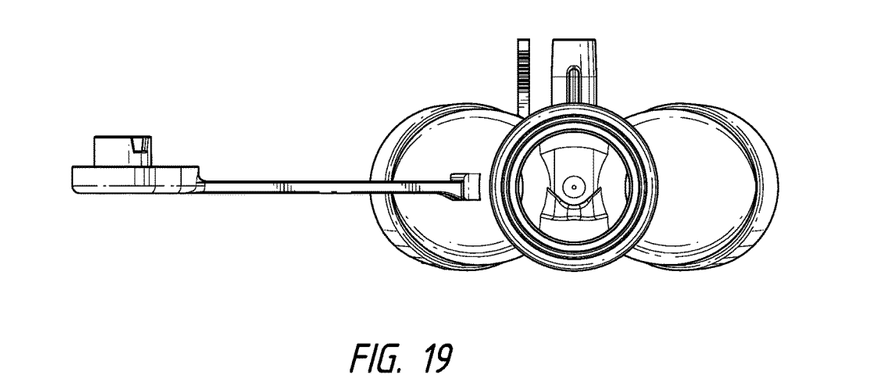
FIG. 19 is a second end view of the wye connector of FIG. 12.

With reference now to FIG. 2, the patient wye 114 will be described in greater detail. In general, the patient wye 114 is an open, three-flow passage connector. The patient wye 114 places the patient limb 112 of the patient circuit 104 in communication with the inspiratory limb 106 and the expiratory limb 110. As such, the patient wye comprises an inspiratory coupling end 124 and an expiratory coupling end 126. In the configuration of FIG. 2, the inspiratory coupling end 124 and the expiratory coupling end 126 are formed in members that extend generally parallel to each other (see FIG. 4). Other configurations are possible. In other words, the inspiratory connector end 124 can define an inspiratory flow lumen having an inspiratory flow lumen axis and the expiratory connector end 126 can define an expiratory flow lumen having an expiratory flow lumen axis. The inspiratory flow lumen axis and the expiratory flow lumen axis can extend generally parallel to each other. For example, in the configuration of FIG. 12, the illustrated patient wye 114' comprises an inspiratory coupling end 124' and an expiratory coupling end 126' that diverge from each other. The two ends 124' and 126' can diverge by an angle α. In some configurations, the angle α can be as small as about 2° and as large as about 30° but any suitable angle α can be used. By diverging instead of being parallel, connections are more easily made with the conduits.

An inspiratory opening 130 can be positioned on the inspiratory coupling end 124 and an expiratory opening 132 can be positioned on the expiratory coupling end 124. In the illustrated configuration, the inspiratory opening 130 is disposed at the end of the inspiratory coupling end 124. In the illustrated configuration, the inspiratory opening 130 is centered on a flow axis of the inspiratory coupling end 124. In the illustrated configuration, the expiratory opening 132 is disposed at the end of the expiratory coupling end 126. In the illustrated configuration, the expiratory opening 132 is centered on a flow axis of the expiratory coupling end 126.

The inspiratory coupling end 124 can include an inspiratory limb connection surface to which an end of the inspiratory limb can connect. Similarly, the expiratory coupling end 126 can include an expiratory limb connection surface to which an end of the expiratory limb can connect. In some configurations, the connection between the inspiratory limb 106 and the inspiratory coupling end 124 and/or the connection between the expiratory limb 110 and the expiratory coupling end 126 can be established by a pressure or friction fitting. Any other suitable type of fitting also can be used.

The patient wye 114 also comprises a patient coupling end 134. A patient opening 136 can be positioned on the patient coupling end 134.

Figure 11:
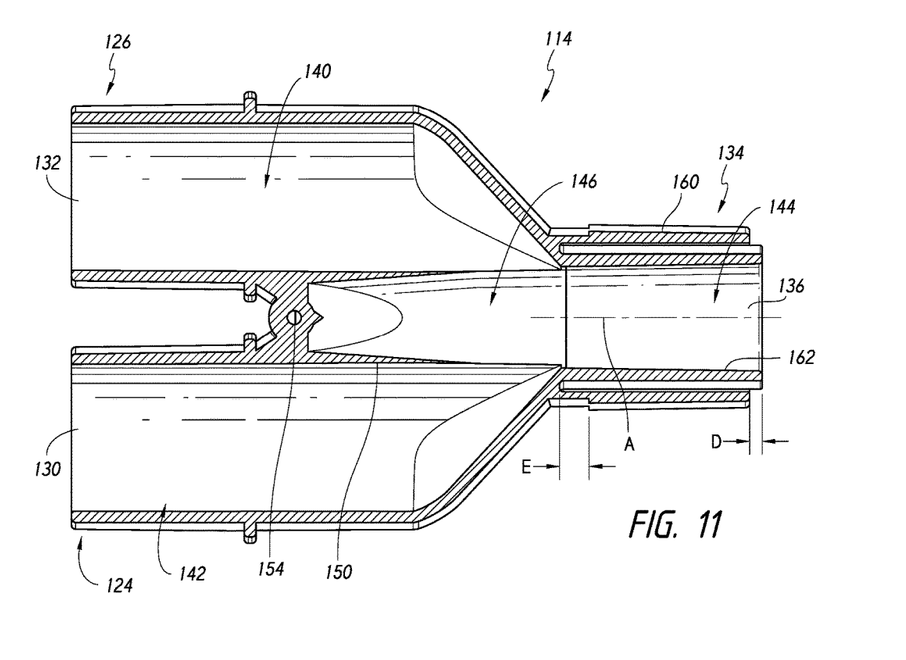
FIG. 11 is a section view of the wye connector of FIG. 2 taken along the line 11-11 in FIG. 9.

As shown in FIG. 11, within the patient wye 114, an inspiratory branch 140, an expiratory branch 142 and a patient branch 144 can be defined. The inspiratory branch 140 and the expiratory branch 142 join with the patient branch 144 in a merge region 146. The merge region 146 can include a portion that is separated from the inspiratory branch 140 and the expiratory branch 142 by a tapering wall 150.

One or more ports can be provided on the patient wye 114. For example, a probe port 152 and an introduction port 154 can be provided. The probe port 152 can be provided such that the probe port 152 intersects with the inspiratory branch 140 while the introduction port 154 can be positioned between the inspiratory branch 140 and the expiratory branch 142 within the portion of the merge region 146 that is substantially surrounded by the wall 150, for example. Other configurations also are possible. The probe port can be positioned between the inspiratory connector end and the patient coupling end. In some configurations, the probe port is positioned along the inspiratory branch. The introduction port can be positioned between the inspiratory connector end and the patient coupling end. In some configurations, the introduction port can be positioned between the inspiratory branch and the expiratory branch.

Figure 10:
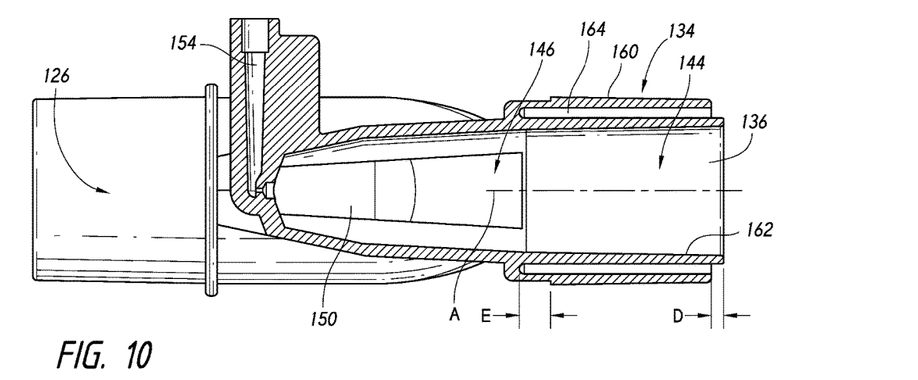
FIG. 10 is a section view of the wye connector of FIG. 2 taken along the line 10-10 in FIG. 9.

With reference now to FIGS. 10 and 11, the patient coupling end 134 will be described in more detail. The patient coupling end 134 comprises a first connector portion 156 that includes a first connector surface 160 and a second connector portion 158 that includes a second connector surface 162. In some configurations, the patient coupling end 134 merely comprises a first connector surface 160 and a second connector surface 162 that are formed on the same connector portion (e.g., inner and outer surfaces).

The first connector surface 160 can be formed as a portion of a male connector while the second connector surface 162 can be formed as a portion of a female connector. In the illustrated configuration, the first connector surface 160 extends around the second connector surface 162. In the illustrated configuration, the first connector surface 160 defines a male taper connector while the second connector surface 162 defines a female taper connector. In some configurations, the first connector surface 160 defines a 22 mm male taper connector while the second connector surface 162 defines a 15 mm female taper connector. In the illustrated configuration, the first connector surface 160 and the second connector surface 162 are symmetrically disposed about an axis A. In some such configurations, the first connector surface 160 has a first diameter at an axial location along the patient coupling end 134 and the second connector surface 162 has a second diameter at the same axial location along the patient coupling end 134 with the first diameter being larger than the second diameter.

With continued reference to FIGS. 10 and 11, a gap 164 can be defined between the first connector portion 156 and the second connector portion 158. The illustrated gap 164 is isolated from any flow within the wye 114. In some configurations, one or more airflow path can be provided in a proximal portion of the second connector portion, which path would be covered by a male connector that joins with the second connector surface and, therefore, would not cause system leaks during use.

In some configurations, all or at least a part of the gap can be solid or contain ribs. In some such configurations, the ribs can be axial ribs, radial ribs or ribs having other configurations. Advantageously, however, the gap 164 is generally void. The gap 164 allows movement or flexing of the two surfaces 160, 162 relative to each other. While movement relative to each other is less important (because both surfaces are not likely to be used at the same time), the ability of each surface to accommodate some relative movement is desirable. The gap 164, therefore, improves the flexibility of the connector surfaces 160, 162 while facilitating the large difference in diameters between the two connector surfaces 160, 162.

In some configurations, the outer first connector surface 160 terminates proximally of a distal-most end of the gap 164. In the illustrated configuration, the outer connector surface 160 terminates proximally of the gap 164. In the illustrated configuration, a distance E can be defined between the distal-most end of the gap 164 and the distal-most end of the outer connector surface 160. In some configurations, the distance E can be between about 0.5 mm and about 15 mm. Preferably, the distance E can be between about 1 mm and about 5 mm. More preferably, the distance E is about 3.6 mm. Other configurations are possible.

In some configurations, the second connector surface 162 terminates proximally of the first connector surface 160. In other words, the inner connector surface 162 projects in an axial direction proximally outward beyond the outer connector surface 160. While, in the illustrated configuration, the entire second connector portion 158 extends proximally beyond the first connector portion 156, in some configurations, only a portion of the second connector portion 158 may extend beyond the first connector portion 156. By projecting beyond the first connector portion 156, the projecting portion can attract attention to the existence of the second connector portion 158. In some configurations, at least a portion of the second connector portion 158 can project proximally of the first connector portion 156 by a distance D. The distance D can be between about 0.1 mm and about 8 mm. Preferably, the distance D can be between about 0.1 mm and about 2 mm. More preferably, the distance D is about 1.8 mm. In one configuration, the distance D is about 0.13 mm (about 5 mils).

Unless the context clearly requires otherwise, throughout the description, the words "comprise", "comprising", and the like, are to be construed in an inclusive sense as opposed to an exclusive or exhaustive sense, that is to say, in the sense of "including, but not limited to."

Although this invention has been described by way of example and with reference to possible embodiments thereof, it is to be understood that modifications or improvements may be made thereto without departing from the scope of the invention. The invention may also be said broadly to consist in the parts, elements and features referred to or indicated in the specification of the application, individually or collectively, in any or all combinations of two or more of said parts, elements or features. Furthermore, where reference has been made to specific components or integers of the invention having known equivalents, then such equivalents are herein incorporated as if individually set forth.

Any discussion of the prior art throughout the specification should in no way be considered as an admission that such prior art is widely known or forms part of common general knowledge in the field.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A wye connector comprising a patient coupling end, the patient coupling end having a first connector surface and a second connector surface, the first connector surface having a first diameter at an axial location along the patient coupling end, the second connector surface having a second diameter at the same axial location along the patient coupling end, the first diameter being larger than the second diameter, and at least a portion of the second connector surface projecting axially outward beyond the first connector surface, wherein the first connector surface is formed on a first connector portion configured to connect to a first connector at the patient coupling end and the second connector surface is formed on a second connector portion configured to connect to a second connector at the patient coupling end, the first connector being a different type of connector than the second connector.

2. The wye connector of claim 1, wherein the first connector portion and the second connector portion are separated by a gap.

3. The wye connector of claim 2, wherein the first connector surface terminates proximally of a distal end of the gap.

4. The wye connector of claim 2, wherein the gap is isolated from flow through the patient coupling end of the wye connector.

5. The wye connector of claim 1, wherein the first connector surface comprises a male taper connector and the second connector surface comprises a female taper connector.

6. The wye connector of claim 5, wherein the male taper connector is a 22 mm male taper connector and the female taper connector is a 15 mm female taper connector.

7. The wye connector of claim 1, further comprising an inspiratory connector end and an expiratory connector end, the inspiratory connector end defining at least a portion of an inspiratory branch and the expiratory connector end defining at least a portion of an expiratory branch.

8. The wye connector of claim 7, wherein the inspiratory connector end defines an inspiratory flow lumen having an inspiratory flow lumen axis and the expiratory connector end defines an expiratory flow lumen having an expiratory flow lumen axis, the inspiratory flow lumen axis and the expiratory flow lumen axis extending generally parallel to each other.

9. The wye connector of claim 7, further comprising a probe port positioned between the inspiratory connector end and the patient coupling end.

10. The wye connector of claim 9, wherein the probe port is positioned along the inspiratory branch.

11. The wye connector of claim 7, further comprising an introduction port positioned between the inspiratory connector end and the patient coupling end.

12. The wye connector of claim 11, wherein the introduction port is positioned between the inspiratory branch and the expiratory branch.

13. The wye connector of claim 1, wherein a first distance from a proximal-most end of the second connector surface to a proximal-most end of the first connector surface is between about 0.1 mm and about 8 mm.

14. The wye connector of claim 13, wherein the first distance is between about 0.1 mm and about 2 mm.

15. The wye connector of claim 14, wherein the first distance is about 0.13 mm.

16. The wye connector of claim 3, wherein a second distance from a distal-most end of the first connector surface to a distal-most end of the gap is between about 0.5 mm and about 15 mm.

17. The wye connector of claim 16, wherein the second distance is between about 1 mm and about 5 mm.

18. The wye connector of claim 17, wherein the second distance is about 3.6 mm.

19. The wye connector of claim 7, wherein the inspiratory connector end defines an inspiratory flow lumen having an inspiratory flow lumen axis and the expiratory connector end defines an expiratory flow lumen having an expiratory flow lumen axis, the inspiratory flow lumen axis and the expiratory flow lumen axis separated from each other by an angle greater than 0 degrees and less than 90 degrees.

20. The wye connector of claim 19, wherein the angle is between about 2 degrees and about 30 degrees.

21. The wye connector of claim 20, wherein the angle is about 14 degrees.

22. The wye connector of claim 2, wherein the first connector surface comprises a male taper connector and the second connector surface comprises a female taper connector.

* * * * *